United States Patent
Hong et al.

(10) Patent No.: US 9,061,072 B2
(45) Date of Patent: Jun. 23, 2015

(54) LIQUID FORMULATION OF LONG-ACTING HUMAN GROWTH HORMONE CONJUGATE

(75) Inventors: Sung Hee Hong, Suwon-si (KR); Byung Sun Lee, Seoul (KR); Dae Seong Im, Yogin-si (KR); Jae Min Lee, Seoul (KR); Sung Min Bae, Seongnam-si (KR); Se Chang Kwon, Seoul (KR)

(73) Assignee: HANMI SCIENCE CO., LTD, Hwaseong-si (KR)

( * ) Notice: Subject to any disclaimer, the term of this patent is extended or adjusted under 35 U.S.C. 154(b) by 0 days.

(21) Appl. No.: 13/809,783

(22) PCT Filed: Jul. 14, 2011

(86) PCT No.: PCT/KR2011/005194
§ 371 (c)(1),
(2), (4) Date: Jan. 11, 2013

(87) PCT Pub. No.: WO2012/008779
PCT Pub. Date: Jan. 19, 2012

(65) Prior Publication Data
US 2013/0115231 A1    May 9, 2013

(30) Foreign Application Priority Data
Jul. 14, 2010  (KR) .................. 10-2010-0067796

(51) Int. Cl.
| | | |
|---|---|---|
| C07K 17/06 | (2006.01) | |
| A61K 39/00 | (2006.01) | |
| A61K 47/48 | (2006.01) | |
| A61K 9/00 | (2006.01) | |
| A61K 9/08 | (2006.01) | |
| A61K 38/27 | (2006.01) | |
| A61K 47/26 | (2006.01) | |
| A61K 47/12 | (2006.01) | |

(52) U.S. Cl.
CPC ......... *A61K 47/48415* (2013.01); *A61K 9/0019* (2013.01); *A61K 9/08* (2013.01); *A61K 38/27* (2013.01); *A61K 47/26* (2013.01); *A61K 47/48215* (2013.01); *C07K 2319/30* (2013.01); *A61K 47/12* (2013.01); *A61K 47/48369* (2013.01)

(58) Field of Classification Search
CPC .... C07K 2319/30; C07K 14/61; A61K 38/27; A61K 9/08; A61K 2039/505; A61K 2300/00
See application file for complete search history.

(56) References Cited

U.S. PATENT DOCUMENTS

| | | | | |
|---|---|---|---|---|
| 7,736,653 | B2* | 6/2010 | Kim et al. | .............. 424/178.1 |
| 8,338,374 | B2* | 12/2012 | Wadhwa et al. | .............. 514/11.4 |
| 2001/0007858 | A1 | 7/2001 | O'Connor et al. | |
| 2004/0180054 | A1 | 9/2004 | Kim et al. | |
| 2006/0183197 | A1 | 8/2006 | Andersen et al. | |
| 2006/0269553 | A1 | 11/2006 | Kim et al. | |
| 2008/0125356 | A1 | 5/2008 | Wadhwa et al. | |
| 2010/0172862 | A1 | 7/2010 | Correia et al. | |

FOREIGN PATENT DOCUMENTS

| | | | | |
|---|---|---|---|---|
| CN | 1723219 | A | 1/2006 | |
| CN | 1761684 | A | 4/2006 | |
| EP | 0938902 | A1 | 9/1999 | |
| KR | 10-0537260 | * | 3/2005 | ............... A61K 9/08 |
| KR | 10-05237260 | B1 | 12/2005 | |
| KR | 10-0567902 | B1 | 4/2006 | |
| KR | 10-0725315 | B1 | 5/2007 | |
| WO | 93/19776 | A1 | 10/1993 | |
| WO | 94/03198 | A1 | 2/1994 | |
| WO | 2006/107124 | A1 | 10/2006 | |
| WO | 2010/011096 | A2 | 1/2010 | |

OTHER PUBLICATIONS

English translation of KR-10-0537260, Mar. 10, 2005.*
Intellectual Property Office of Taiwan, Communication dated Jun. 4, 2013 issued in the corresponding Taiwanese Patent Application No. 100125060.
The State Intellectual Property Office of P.R.C., Communication dated Apr. 1, 2014, issued in corresponding Chinese application No. 201180039263.8.
Australian Patent Office, Communication dated Oct. 8, 2014 issued in counterpart application No. 2011277203.

* cited by examiner

*Primary Examiner* — Elly-Gerald Stoica
(74) *Attorney, Agent, or Firm* — Sughrue Mion, PLLC

(57) ABSTRACT

Disclosed is a liquid formulation of long-acting human growth hormone (hGH) conjugate, free of albumin, which can guarantee the stability of the long-acting hGH conjugate when stored over a long period of time, wherein the long-acting human growth hormone conjugate includes a human growth hormone linked to an immunoglobulin Fc region, and has a prolonged in vivo stability compared to the native form. The liquid formulation of hGH conjugate including a pH 5.0~6.0 buffer, a sugar alcohol, a salt and a non-ionic surfactant is free of human serum albumin and other hazardous factors which are potentially contaminated with viruses, and can provide excellent storage stability customized for a long-acting hGH conjugate composed of an hGH polypeptide and an immunoglobulin Fc region which has higher molecular weight and in vivo durability, compared to the native.

21 Claims, 2 Drawing Sheets

LIQUID FORMULATION OF LONG-ACTING HUMAN GROWTH HORMONE CONJUGATE

CROSS REFERENCE TO RELATED APPLICATIONS

This application is a National Stage of International Application No. PCT/KR2011/005194, filed on Jul. 14, 2011, which claims priority from Korean Patent Application No. 10-2010-0067796, filed Jul. 14, 2010, the contents of all of which are incorporated herein by reference in their entirety.

TECHNICAL FIELD

The present invention relates to a liquid formulation of long-acting human growth hormone conjugate, free of albumin, which can guarantee the stability of the long-acting human growth hormone conjugate when stored over a long period of time, wherein the long-acting human growth hormone conjugate comprises a human growth hormone linked to an immunoglobulin Fc region, and has a prolonged in vivo stability compared to the native form.

BACKGROUND ART

Human growth hormone (hereinafter referred to as "hGH") is an aglycosylated peptide hormone that is secreted from the anterior pituitary gland and interacts with a specific receptor on the cell surface in various tissues so as to simulate the secretion of other growth factors, to account for increasing the size of various parts of the body. Ever since discovering that the growth hormone from the human pituitary gland is an effective therapeutic for pituitary dwarfism, hGH demand has increased explosively. However, the supply of hGH that can be extracted from the human pituitary gland is very limited. Further, after the incidence of the degenerative neurological disorder Creutzfeldt-Jacob disease in children who received cadaver-derived hGH, the FDA in the United States of America has banned the use of the hGH extracted from the pituitary glands of a cadaver, based on the assumption that infectious prions that caused the disease were transferred along with the cadaver-derived hGH (Roger, L., Science 234: 22, 1986). Currently, the biosynthetic human growth hormone produced by *E. coli* using gene recombination technology is commercially available with the approval of the FDA.

Polypeptides, such as hGH, are apt to degenerate due to their low stability, and are readily degraded by serum proteases and removed by the kidney or the liver. Hence, drugs containing polypeptides as pharmaceutically active ingredients have to be frequently administered to patients in order to maintain serum levels and titers thereof. However, the maintenance high serum levels of active polypeptides by frequent administration of protein drugs, which are in the form of injections in most cases, is painful to patients.

To solve these problems, attempts have been made towards maximizing medicinal effects by improving serum stability of protein drugs and maintaining a high serum level of protein drugs for a long period. Therefore, formulations of protein drugs that have increased stability and activity maintained at sufficiently high levels without inducing immune responses in patients, is needed.

For stabilizing proteins and preventing contact with protease and renal loss, conventionally, highly soluble polymers, such as polyethylene glycol (PEG), are chemically added to the surface of protein drugs. Being non-specifically conjugated to certain or various sites of target proteins, PEG can increase the solubility of the target proteins, stabilize the proteins and prevent them from being degraded, without causing significant side effects (Sada et al., J. Fermentation Bioengineering, 1991, 71:137-139). PEG conjugation can contribute to the stability of the proteins, but significantly decreases their activity. PEG of higher molecular weight has a lowered reactivity with proteins, thus reducing the yield.

An alternative strategy for increasing the in vivo stability of physically active proteins is by using genetic recombination to fuse the target proteins and the proteins that have high serum stability, which is a process of linking respective genes encoding the proteins to each other and culturing the animal cells transformed with the fused genes. For example, fusion proteins in which albumin or its fragments, known to increase the stability of proteins, fused to target proteins by genetic recombination have been reported (International Patent Publication Nos. WO 93/15199 and WO 93/15200, European Patent Publication No. EP 413,622).

U.S. Pat. No. 5,045,312 discloses that hGH conjugated with bovine serum albumin or murine immunoglobulin using a cross-linking agent has enhanced activity compared to the unmodified growth hormone. The only cross-linking agents mentioned in the patent are low-molecular weight compounds such as carbodiimide or glutaraldehyde. However, such low-molecular weight cross-linking agents do not guarantee homogeneous compositions due to their non-specific linkages, and may be toxic in vivo. Further, this patent revealed only the increase of activity of a growth hormone by chemical coupling, but did not exhibit the effect of chemical coupling on the activity on other polypeptide drugs, with no understanding of the correlation with the stability of proteins such as the increase in durability and serum half-life.

Recently, conjugates made between physiologically active polypeptides with an immunoglobulin Fc region and a non-peptide polymer have been introduced as long-acting formulations which promise protein drugs both in minimal reduction in activity and an increase in stability, as described in Korean Patent No. 10-0567902 (Physiologically Active Polypeptide Conjugate Having Improved In Vivo Durability), and Korean Patent No. 10-0725315 (Protein Complex Using An Immunoglobulin Fragment And Method For The Preparation Thereof).

According to these methods, hGH may be applied as the physiologically active polypeptide such that a long-acting hGH conjugate can be prepared. For these long-acting hGH conjugates to be used as drugs, it is essential that the in vivo medicinal effect of hGH be maintained while suppressing it from undergoing physicochemical changes such as denaturation, aggregation, adsorption or hydrolysis induced by light, heat or impurities in additives. Compared to hGH, a long-acting hGH conjugate is larger in size and molecular weight and thus is more difficult to stabilize.

Generally, proteins have a very short half life, and exhibit denaturation, such as the aggregation of monomers, precipitation by aggregation, and adsorption onto the surface of vessels, upon exposure to inappropriate temperatures, a water-air interface, high pressure, physical or mechanical stress, organic solvents, microbial contamination, etc. Once denatured, proteins lose their inherent physicochemical properties and physiological activity. Since protein denaturation is irreversible in most cases, it is almost impossible for denatured proteins to recover their inherent properties.

Absorbed proteins are apt to aggregate as they denature. The aggregated proteins may act as antigenic materials when injected into the body and, therefore proteins that are sufficiently stable must be administered. Various methods for preventing proteins from denaturing have been studied (John Geigert, J. Parenteral Sci. Tech., 43, No 5, 220-224, 1989, David Wong, Pharm. Tech. October, 34-48, 1997, Wei Wang., Int. J. Pharm., 185, 129-188, 1999, Willem Norde, Adv. Colloid Interface Sci., 25, 267-340, 1986, Michelle et al., Int. J. Pharm. 120, 179-188, 1995).

Some protein drugs adopted a lyophilization process to avoid the stability problems. However, lyophilized products are inconveniently dissolved in solvents for injection. Further, lyophilization requires a mass-scale freeze-drier, increasing the investment cost in the production of the protein drugs. Powdering of proteins with a spray drier was also suggested to maintain the stability of the proteins, but is not economically beneficial due to a low yield. Further, exposure to the high temperatures of spray drying produces negative side-effects on the proteins themselves.

Stabilizers, arising as an alternative approach overcoming these limitations, have been studied because when they are added to protein drug solutions, they have the ability to suppress physicochemical changes of protein drugs and guarantee in vivo medicinal efficacy even after long-term storage. Human serum albumin has been widely used as a stabilizer for various protein drugs, and the performance thereof has been proven (Edward Tarelli et al., Biologicals (1998) 26, 331-346).

When administered with human serum albumin, patients run the risk of being exposed to biological contaminants or pathogens such as mycoplasma, prions, bacteria and viruses because although the process used to purify albumin comprises the inactivation, screening or inspection of such biological contaminants or pathogens, these cannot be perfectly eliminated or inactivated. For example, a screening process comprises the inspection of donor's serum for certain viruses, but the inspection is not always reliable. Particularly, a very small number of certain viruses, if present, cannot be detected.

Due to their chemical differences, different proteins may be gradually inactivated at different rates under different conditions during storage. That is to say, the extension of the storage term by a stabilizer is not identical for different proteins. For this reason, stabilizers to be used vary in ratio to target proteins, concentration, and type depending on the physicochemical properties of the target proteins. Contrary to expectations, stabilizers, when used in combination, may bring about negative effects because of competition and interaction therebetween. Further, since the nature or concentration of target proteins may change during storage, the stabilizers used may provide effects different from those intended. Thus, a great amount effort and precautions are required to stabilize proteins in solutions.

Particularly, long-acting hGH conjugates that are prepared by linking the physiologically active peptide hGH with immunoglobulin Fc regions to improve the in vivo durability and stability of hGH require special compositions for stabilizing the protein because they are quite different in molecular weight and size from typical hGH.

International Patent Publication No. WO93/19776 discloses a stable liquid formulation of hGH comprising a buffer of pH 6.0~7.0, an amino acid, mannitol and optionally a preservative such as benzyl alcohol. International Patent Publication No. WO94/03198 discloses a stable liquid formulation containing hGH, a buffer of pH 6.0, a non-ionic surfactant, a preservative, and, optionally, a neutral salt or mannitol. U.S. Pat. No. 6,448,225 discloses a stable pharmaceutically acceptable liquid formulation containing hGH, a buffer of pH 6.0, a non-ionic surfactant, and, optionally, a neutral salt or mannitol, with no glycine requirement. Korean Patent No. 10-0537260 discloses a stabilized liquid formulation of hGH containing PEG, instead of a non-ionic surfactant and a preservative, a buffer and an isotonic agent as active ingredients because non-ionic surfactants and preservatives cause hGH to be deaminated significantly.

However, hGH and an immunoglobulin Fc region, although both are peptides or proteins, have different physicochemical properties, and are both required to be stabilized at the same time. As illustrated above, different proteins may be gradually inactivated at different rates under different conditions during storage due to their chemical differences. Contrary to expectations, the use of stabilizers suitable for use in stabilizing peptides or proteins in combination may bring about negative effects because of the competition and interaction therebetween. Hence, as for long-acting hGH conjugates, the compositions of their stable formulations are different from those of formulations for stabilizing hGH alone. In fact, it is very difficult to discover a formulation for stabilizing both hGH and an immunoglobulin Fc region.

Leading to the present invention, intensive and thorough research into the safe storage of long-acting hGH-immunoglobulin Fc conjugates over a long period of time, conducted by the present inventors, resulted in the finding that a stabilizer composition comprising a buffer of pH 5.0~6.0, a non-ionic surfactant, a sugar alcohol and a salt can provide an economically beneficial liquid formulation with a long-acting hGH conjugate which can give a great boost to increasing the stability of the long-acting hGH conjugate during storage for a long period of time without concerns about viral contamination.

DISCLOSURE

Technical Problem

It is therefore an object of the present invention to provide a liquid formulation of long-acting hGH conjugate comprising a long-acting hGH conjugate, a buffer of pH 5.0~6.0, a sugar alcohol, a salt and a non-ionic surfactant which is improved in storage stability.

Technical Solution

In accordance with an aspect thereof, the present invention provides a liquid formulation of long-acting hGH conjugate comprising a pharmaceutically effective amount of a long-acting hGH conjugate, a buffer of pH 5.0~6.0, a sugar alcohol, a salt and a non-ionic surfactant.

As used herein, the term "long-acting hGH conjugate" is intended to refer to a conjugate in which the physiologically active peptide human growth hormone is linked to an immunoglobulin Fc region and the physiological activity of which is of increased duration compared to native hGH.

The term "long-acting," as used herein, is intended to mean that the physiological activity has a longer duration than native hGH.

The hGH useful in the present invention has an amino acid sequence of the wild-type or a closely related analog having an activity similar to that of the wild-type. Any hGH, whether native or recombinant, may be used in the present invention. Preferred is the recombinant hGH that is prepared using *E. coli* as a host. As long as its biological activity is not significantly changed, any mutant derived from native hGH by the substitution, deletion or insertion of amino acid residues may be used in the art.

As for the immunoglobulin Fc useful in the present invention, it may be human immunoglobulin Fc or its closely related analog or may originate from animals such as cow, goats, pigs, mice, rabbits, hamsters, rats, guinea pigs, etc. The immunoglobulin Fc region may be derived from IgG, IgA, IgD, IgE, IgM, or combinations or hybrids thereof. The immunoglobulin Fc region may be a hybrid Fc region of different domains of immunoglobulins selected from the group consisting of IgG, IgA, IgD, IgE, and IgM, or may be a dimer or multimer of a single chain immunoglobulin having domains of the same origin. Preferred is an Fc region derived from IgG or IgM, which are those that are the most abundant inhuman blood, with the greatest preference for an Fc region derived IgG, known to improve the serum half-life of the ligand-binding proteins. Immunoglobulin Fc may be obtained by the treatment of native IgG with a certain protease or produced from a transformed cell using genetic recombination technology. Preferably, the immunoglobulin Fc is a recombinant human immunoglobulin Fc produced in *E. coli*.

IgG is divided into the IgG1, IgG2, IgG3 and IgG4 subclasses, and the present invention may include combinations or hybrids thereof. Preferred are the IgG2 and IgG4 subclasses, and most preferred is the Fc region of IgG4 rarely having effector functions such as CDC (Complement Dependent Cytotoxicity). That is, the immunoglobulin Fc region most suitable as the drug carrier of the present invention is a human IgG4-derived aglycosylated Fc region. The human-derived Fc region is more preferable than a non-human derived Fc region, which may act as an antigen in the human body and cause undesirable immune responses such as the production of a new antibody against the antigen.

The long-acting hGH conjugate used in the present invention may be prepared by linking the hGH to an immunoglobulin Fc region produced by the above-mentioned method. The linking method may be achieved by cross-linking hGH to an immunoglobulin Fc region via a non-peptidyl polymer or by producing a fusion protein in which hGH is fused to an immunoglobulin Fc region using genetic recombination. Preferred is a linkage between hGH and an immunoglobulin Fc region via a non-peptidyl polymer.

The non-peptidyl polymer useful for the cross-linking may be selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (poly (lactic acid) and PLGA (poly (lactic-glycolic acid), lipid polymers, chitins, hyaluronic acid and a combination thereof. The most preferred is polyethylene glycol. Their derivatives well known in the art and derivatives which can be readily prepared using a method known in the art are also within the scope of the present invention.

For preparing long-acting hGH conjugates, reference may be made to Korean Patent No. 0725315 the disclosure of which is hereby incorporated by reference in its entirety. Those skilled in the art can produce the long-acting hGH conjugates of the present invention with reference to the documents.

The liquid formulation of long-acting hGH conjugate of the present invention comprises a long-acting hGH conjugate in a pharmaceutically effective amount. Typically, the pharmaceutically effective amount of hGH corresponds to about 1~3 mg in a single-use vial. The long-acting hGH conjugate used in the present invention ranges in concentration from 1 mg/mL to 55 mg/mL and preferably from 15 mg/mL to 25 mg/mL.

The term "stabilizer," as used herein, is intended to refer to a substance that allows the long-acting hGH conjugate to be stored stably. The term "stabilization" means the loss of less than a certain percentage of an active ingredient, typically less than 10% and preferably less than 5%. A formulation is understood to be stable when the long-acting hGH conjugate retains its activity at a level 90% or greater than the original activity and preferably at a level of about 92~95% after storage at 10±3° C. for two years, 25±2° C. for six months or at 40±2° C. for one to two weeks. With regard to proteins such as long-acting hGH conjugates, their storage stability is very important in suppressing their antigenic forms from being potentially produced as well as guaranteeing accurate doses thereof.

Although held together by the long-acting hGH conjugate of the present invention, the physicochemical properties of the physiologically active peptide hGH and the immunoglobulin Fc region are different from each other and must be stabilized simultaneously. Physicochemical differences therebetween may cause different peptides or proteins to be gradually inactivated at respective rates under different conditions during storage. Contrary to expectations, the use of stabilizers suitable for active peptides or proteins in combination may bring about a negative effect because they compete or interact with each other.

Designed to simultaneously stabilize both the physiologically active peptide hGH and an immunoglobulin Fc region so that the activity of the long-acting hGH conjugate can be maintained at the desired level for a long period of time, the stabilizer of the present invention comprises a specific buffer, a sugar alcohol, a salt and a non-ionic surfactant.

The buffer functions as to maintain the pH of the solution within a predetermined range to prevent a sharp pH change that can lead to the inactivation of the long-acting hGH. As long as it is known in the art as a pharmaceutically acceptable pH buffer, any buffer may be used in the present invention. The buffer useful in the present invention includes an alkaline salt (sodium or potassium phosphate or hydrogen or dihydrogen salts thereof), sodium citrate/citric acid, sodium acetate/acetic acid, and a combination thereof. Preferred are a citrate buffer and a phosphate buffer, with a greater preference for citrate buffer. The citrate buffer useful in the present invention may contain citrate preferably in an amount of from 5 mM to 100 mM and more preferably in a concentration of from 10 mM to 50 mM.

Since a reaction within a solution may vary depending on the pH of the buffer in the solution, the pH of the stabilizer is very important. The pH at which reactions occur and its effect on solubility differ from one protein to another. Hence, it is difficult to stabilize proteins in such a manner that they maintain high solubility and accurate three-dimensional structure without the generation of denatured impurities. Conventional hGH formulations usually employ a buffer with a pH of 6.0~7.0 or higher in order to reduce the generation of impurities and increase the solubility of the protein.

The stabilizer of the present invention comprises a buffer with a pH of 5.0~6.0, preferably with a pH of 5.2~6.0, and more preferably a pH of 5.2~5.5. In an embodiment of the present invention, it was measured after storage for three months that the contents of impurity #6 and #7, corresponding to deaminiated impurities of hGH, were decreased particularly at a low pH (e.g., pH 5.2) (FIG. 1). These data indicate that because the long-acting hGH conjugate composed of hGH and immunoglobulin Fc region is different in property from hGH alone, the liquid formulation designed both to stabilize the long-acting hGH conjugate and to increase the solubility of the long-acting hGH conjugate must be different in pH from conventional liquid formulations of hGH.

In addition, sugar alcohol acts to increase the stability of the long-acting hGH conjugate. In the present invention, sugar alcohol is used preferably in an amount of from 1 to 10% (w/v) and more preferably in an amount of 5% (w/v) based on the total volume of the formulation. Examples of the sugar alcohol useful in the present invention include, but are not limited to, mannitol, sorbitol and a combination thereof. As is understood from the data of Table 4, the addition of 0.5% L-Arg-HCl to mannitol has no influence on the stability of the long-acting hGH conjugate.

The salt has the effect of further stabilizing the long-acting hGH conjugate in solution as well as acting as an isotonic agent that maintains the proper osmotic pressure when a solution of the hGH conjugate is being injected into the body. The salt is typically a water-soluble inorganic salt and preferably sodium chloride.

In the formulation, the salt may be present preferably in an amount of from 5 to 200 mM and more preferably in an amount of 150 mM, and its content may be adjusted according to the type and amount of the ingredients so that the formulation is isotonic.

In an embodiment of the present invention, the long-acting hGH conjugate was evaluated for stability in formulations comprising a buffer with a pH of 5.0~6.0, a sugar alcohol and a non-ionic surfactant in the presence or absence of a salt. As a result, the stability of the long-acting hGH conjugate was maintained at a remarkably higher level when it was stored at 25° C. for four weeks in a formulation containing 5% mannitol in the presence of NaCl, particularly 150 mM NaCl than in the absence of NaCl (Table 2). In contrast to conventional hGH, the long-acting hGH conjugate according to the present invention can be stabilized in a formulation containing 1~10% (w/v) sugar alcohol and 5~200 mM NaCl and further stabilized in a formulation containing a buffer with a pH of 5.0~6.0, a sugar alcohol, a non-ionic surfactant and a salt.

The non-ionic surfactant reduces the surface tension of the protein solution to prevent the absorption or aggregation of proteins onto a hydrophobic surface. Examples of the non-ionic surfactant useful in the present invention include polysorbates, poloxamers and combinations thereof, with preference for polysorbates. Among the non-ionic surfactants of polysorbates are polysorbate 20, polysorbate 40, polysorbate 60 and polysorbate 80. Preferred is polysorbate 80.

According to an embodiment of the present invention, the stability of the long-acting hGH conjugate was observed to increase in the presence of polysorbate 80 (Table 8). The stability of the long-acting conjugate was the same when polysorbate 20 was used instead of polysorbate 80 until two weeks had passed, but after storage for four weeks, there is a significant difference in the stability therebetween although the surfactants are very similar to each other.

In the liquid formulation of the present invention, the non-ionic surfactant is contained preferably in an amount of 0.1% (w/v) or less, more preferably in an amount of from 0.001 to 0.05% (w/v), and far more preferably in an amount of 0.005% (w/v). Norditropin, a liquid formulation of hGH commercially available from Nordisk, employs 3 mg/mL Poloxamer 188 as a surfactant (Table 9). According to an embodiment of the present invention, the long-acting hGH conjugates in the formulation containing 3 mg/mL poloxamer 188 were observed to aggregate after storage at 25° C. for two weeks (Table 8). These data imply that the type and concentration of the surfactant, acting as a stabilizer for protein drugs, must be drug specific.

In an embodiment of the present invention, a formulation containing of 1~10% (w/v) of sugar alcohol and 5~200 mM of NaCl in addition to a pH 5.2 buffer and an non-ionic surfactant was found to significantly increase the storage stability of the long-acting hGH conjugate, indicating that a combination of a pH 5.2 buffer, a non-ionic surfactant, a sugar alcohol and a salt shows a synergistic effect on the stability of the long-acting hGH conjugate.

It is preferred that the stabilizer of the present invention not contain albumin. Because it is produced from human serum, there is always the possibility that human serum albumin available as a stabilizer for proteins may be contaminated with pathogenic viruses of human origin. Gelatin or bovine serum albumin may cause diseases or may be apt to induce an allergic response in some patients. Free of heterologous proteins such as serum albumins of human or animal origin or purified gelatin, the stabilizer of the present invention has no possibility of causing viral contamination.

In addition to the pH 5.0~6.0 buffer, the salt, the sugar alcohol and the non-ionic surfactant, the liquid formulation of the present invention may further comprise ingredients or materials well known in the art unless they degrade the effect of the present invention. For example, the formulation of the present invention may further comprise sugars, polyalcohols or neutral amino acids.

Preferable examples of the sugars that may be further contained in the formulation to increase the storage stability of the long-acting conjugate include monosaccharides such as mannose, glucose, fucose and xylose, and polysaccharides such as lactose, sucrose, raffinose and dextran. Among the polyalcohols that can be additionally used in the present invention are propylene glycol, low-molecular weight polyethylene glycol, glycerol, low-molecular weight polypropylene glycol, and a combination thereof. Based on the total volume of the formulation, each of the sugar and the polyalcohol may be used in an amount of from 1 to 10% (w/v) and preferably in an amount of 5% (w/v).

According to a preferred embodiment thereof, the present invention provides a liquid formulation comprising a 20 mM Na-citrate buffer (pH 5.2~6.0), 5~200 mM NaCl, 1~10% (w/v) mannitol, and 0.001~0.05% polysorbate 80. In an embodiment of the present invention, a liquid formulation of long-acting hGH conjugate comprising an Na citrate buffer, pH 5.2, 5% (w/v) mannitol, 150 mM NaCl and 0.005% (w/v) polysorbate 80 was compared with Norditropin, an hGH formulation commercially available from Nordisk. The liquid formulation of long-acting hGH conjugate of the present invention exhibited storage stability as high as or higher than that of Norditropin (Table 10). In a test for long-term storage stability according to another embodiment, the liquid formulation of long-acting hGH conjugate of the present invention was found to maintain the activity of the long-acting hGH conjugate at high levels for six months (Table 11).

Having no concomitant danger of viral contamination as well as being simple and having excellent storage stability, the albumin-free, liquid formulation of long-acting hGH conjugate of the present invention, which is designed to provide stability for the long-acting hGH conjugate, has an economical benefit compared to other stabilizers or freeze-drying agents.

In addition, because it comprises a long-acting hGH conjugate which has higher in vivo durability than does the native form, the liquid formulation of the present invention allows the activity of the protein to be maintained at high levels for a long period of time, compared to typical hGH formulations, and thus can be used as an effective drug formulation.

Advantageous Effects

The liquid formulation of hGH conjugate comprising a pH 5.0~6.0 buffer, a sugar alcohol, a salt and a non-ionic surfactant in accordance with the present invention is free of human serum albumin and other hazardous factors which are potentially contaminated with viruses, and can provide excellent storage stability customized for a long-acting hGH conjugate composed of an hGH polypeptide and an immunoglobulin Fc region which has higher molecular weight and in vivo durability, compared to the native.

DESCRIPTION OF DRAWINGS

The above and other objects, features and other advantages of the present invention will be more clearly understood from the following detailed description taken in conjunction with the accompanying drawings, in which.

MODE FOR INVENTION

Figure 1:
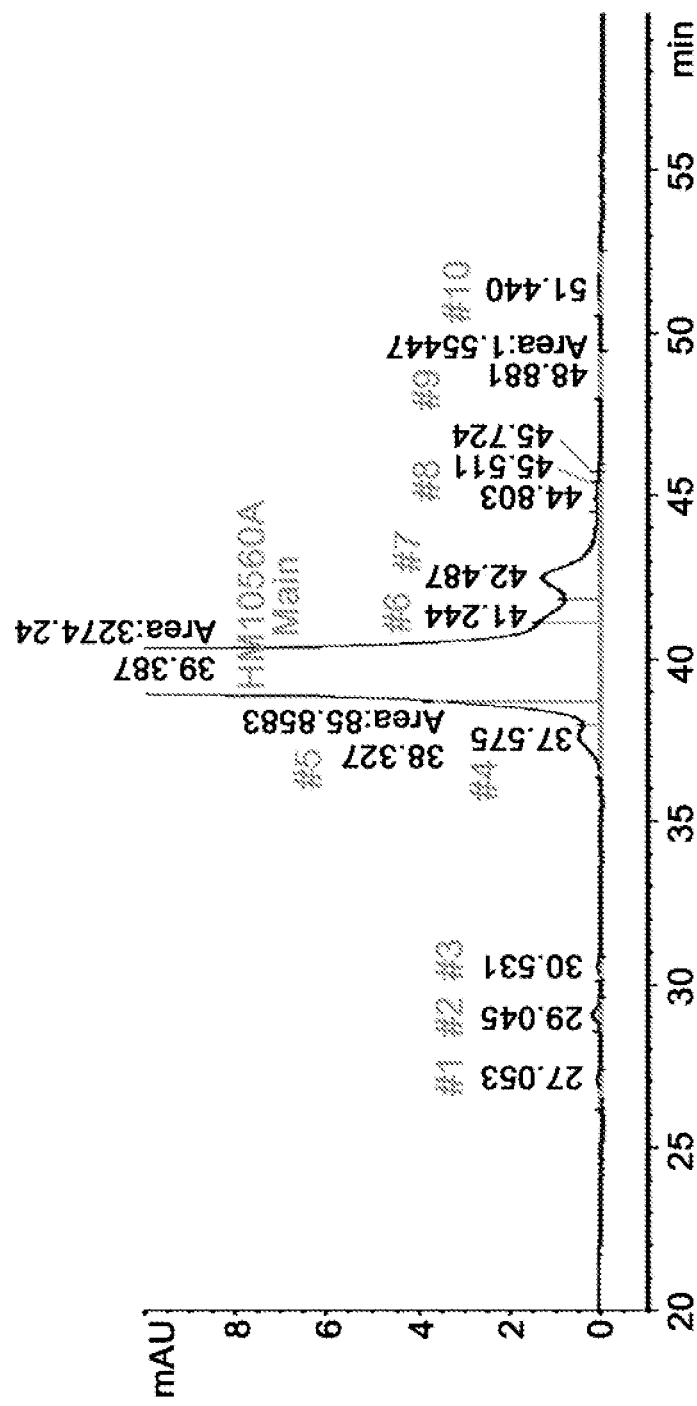
FIG. 1 is a representative IE-HPLC chromatogram obtained after a long-acting hGH conjugate was analyzed for stability by IE-HPLC during the storage thereof at 4° C. for three months in a buffer at various pH values as described in Example 4.

A better understanding of the present invention may be obtained through the following examples which are set forth to illustrate, but are not to be construed as limiting the present invention.

Example 1

Preparation of Long-Acting hGH Conjugate

ALD-PEG-ALD (IDB), which is a 3.4 kDa polyethylene glycol with an aldehyde group at each end, was conjugated with hGH (Mw 22 kDa) and then linked to the N-terminus of a human IgG4-derived aglycosylated Fc region (Mw 50 kDa), followed by purification to afford an hGH-PEG-Fc conjugate.

Example 2

Assay of Long-Acting hGH Conjugate for Stability in the Presence or Absence of Salt To evaluate the stability of the long-acting hGH conjugate in the formulation comprising a buffer, a sugar alcohol and a non-ionic surfactant in the presence or absence of a salt, the long-acting hGH conjugate was stored at 25° C. for four weeks in the formulation of Table 1 below and then its stability was analyzed using ion exchange chromatography (IEC) and size exclusion chromatography (SEC). In the formulation, citrate buffer was used as the buffer, mannitol as the sugar alcohol, and polysorbate 80 as the non-ionic surfactant. In Table 2, IE-HPLC (%) and SE-HPLC (%) is represented by (Area %/Start Area %), showing the residual purity of the long-acting hGH conjugate in comparison with initial purity.

TABLE 1

| No. | Conc. | Buffer | Salt | Sugar alcohol | Surfactant |
| --- | --- | --- | --- | --- | --- |
| 1 | 19.5 mg/mL | 20 mM Na-Citrate (pH 5.2) | 150 mM NaCl | 5% Mannitol | 0.005% Polysorbate 80 |

TABLE 1-continued

| No. | Conc. | Buffer | Salt | Sugar alcohol | Surfactant |
| --- | --- | --- | --- | --- | --- |
| 2 | 19.5 mg/mL | 20 mM Na-Citrate (pH 5.2) | — | 5% Mannitol | 0.005% Polysorbate 80 |

TABLE 2

| | IE-HPLC (%) | | | | SE-HPLC (%) | | | |
| --- | --- | --- | --- | --- | --- | --- | --- | --- |
| No. | Start | 1 week | 2 weeks | 4 weeks | Start | 1 week | 2 weeks | 4 weeks |
| 1 | 100 | 94.5 | 92.5 | 85.0 | 100 | 98.5 | 98.4 | 93.9 |
| 2 | 100 | 94.7 | 90.7 | 80.9 | 100 | 98.9 | 98.1 | 93.6 |

As is understood from the data, the stability of the long-acting hGH conjugate was maintained at a remarkably higher level when it was stored at 25° C. for four weeks in a formulation containing 5% mannitol in the presence of NaCl, particularly 150 mM NaCl, compared to in the absence of NaCl.

Example 3

Assay of Long-Acting hGH Conjugate for Stability in Relation to Sugar Alcohol

During the storage of the long-acting hGH in a formulation comprising a buffer as a stabilizer, NaCl as an isotonic agent, a non-ionic surfactant, and a sugar alcohol, the effect of the sugar alcohol on the stability of the long-acting hGH was examined.

In the formulation, a citric acid buffer (sodium citrate, pH 5.2) was used as the buffer, mannitol or sorbitol as the sugar alcohol, and polysorbate 80 as the non-ionic surfactant.

The long-acting hGH conjugate was stored at 25° C. for four weeks in the formulations of Table 3 below and then its stability was analyzed using ion exchange chromatography (IEC) and size exclusion chromatography (SEC). In Table 4, IE-HPLC (%) and SE-HPLC (%) is represented by (Area %/Start Area %), showing the residual purity of the long-acting hGH conjugate in comparison with initial purity.

TABLE 3

| No. | Conc. | Buffer | Salt | Sugar Alcohol | Surfactant |
| --- | --- | --- | --- | --- | --- |
| 1 | 19.5 mg/mL | 20 mM Na-Citrate (pH 5.2) | 150 mM NaCl | 5% Mannitol | 0.005% Polysorbate 80 |
| 2 | 19.5 mg/mL | 20 mM Na-Citrate (pH 5.2) | 150 mM NaCl | 5% Sorbitol | 0.005% Polysorbate 80 |
| 3 | 19.5 mg/mL | 20 mM Na-Citrate (pH 5.2) | 150 mM NaCl | 5% Mannitol 0.5% Arg-HCl | 0.005% Polysorbate 80 |

TABLE 4

| | IE-HPLC (%) | | | | SE-HPLC (%) | | | |
|---|---|---|---|---|---|---|---|---|
| No. | Start | 1 week | 2 week | 4 week | Start | 1 week | 2 week | 4 week |
| 1 | 100 | 98.8 | 97.6 | 94.7 | 100 | 96.0 | 100 | 99.9 |
| 2 | 100 | 98.6 | 97.4 | 94.6 | 100 | 100 | 99.9 | 99.9 |
| 3 | 100 | 98.8 | 97.8 | 94.6 | 100 | 99.6 | 99.4 | 99.3 |

As can be seen in the above tables, stability of the sugar alcohols mannitol and sorbitol was similar. Also, the addition of 0.5% L-Arg-HCl to mannitol had no influence on the stability of the long-acting hGH conjugate.

Example 4

Assay of Long-Acting hGH Conjugate for Stability in Relation to pH of Buffer

The stability of the long-acting hGH was evaluated in a buffer at various pH values. In this context, the long-acting hGH conjugate was stored at 4° C. for three months in the formulations of Table 5 below and then its stability was analyzed using ion exchange chromatography (IEC). In Table 6, IE-HPLC (%) is expressed as (Area %/Start Area %), showing the residual purity of the long-acting hGH conjugate and impurities in comparison with initial purity as a main peak and impurity peaks, respectively (FIG. 1).

TABLE 5

| No. | Conc. | Buffer | Salt | Sugar Alcohol | Surfactant |
|---|---|---|---|---|---|
| 1 | 19.5 mg/mL | 20 mM Na-Citrate (pH 5.2) | 150 mM NaCl | 5% Mannitol | 0.005% Polysorbate 80 |
| 2 | 19.5 mg/mL | 20 mM Na-Citrate (pH 5.5) | 150 mM NaCl | 5% Mannitol | 0.005% Polysorbate 80 |
| 3 | 19.5 mg/mL | 20 mM Na-Citrate (pH 6.0) | 150 mM NaCl | 5% Mannitol | 0.005% Polysorbate 80 |

TABLE 6

| | | IE-HPLC (%) | | | | | | | | | |
|---|---|---|---|---|---|---|---|---|---|---|---|
| No. | Time | #1 | #2 | #3 | #4 | #5 | Main Peak | #6 | #7 | #8 | #9 | #10 |
| 1 | 0M | 0.0 | 0.0 | 0.0 | 0.0 | 0.0 | 96.6 | 1.4 | 1.5 | 0.3 | 0.1 | 0.1 |
|   | 2M | 0.1 | 0.1 | 0.0 | 0.2 | 0.0 | 93.6 | 2.3 | 3.1 | 0.3 | 0.0 | 0.1 |
|   | 3M | 0.1 | 0.2 | 0.1 | 0.4 | 0.0 | 92.7 | 1.9 | 3.8 | 0.4 | 0.0 | 0.2 |
| 2 | 0M | 0.0 | 0.0 | 0.0 | 0.0 | 0.0 | 96.5 | 1.4 | 1.6 | 0.3 | 0.1 | 0.1 |
|   | 2M | 0.1 | 0.4 | 0.1 | 0.0 | 0.0 | 93.9 | 2.1 | 3.0 | 0.3 | 0.1 | 0.2 |
|   | 3M | 0.1 | 0.2 | 0.0 | 0.2 | 0.0 | 92.4 | 2.1 | 4.2 | 0.5 | 0.0 | 0.1 |
| 3 | 0M | 0.0 | 0.0 | 0.0 | 0.0 | 0.0 | 96.2 | 1.4 | 1.8 | 0.3 | 0.1 | 0.2 |
|   | 2M | 0.1 | 0.4 | 0.1 | 0.0 | 0.0 | 93.8 | 2.0 | 3.3 | 0.3 | 0.0 | 0.1 |
|   | 3M | 0.1 | 0.2 | 0.0 | 0.0 | 0.0 | 92.3 | 2.1 | 4.7 | 0.4 | 0.0 | 0.1 |

After storage for three months, the contents of impurity #6 and #7 were decreased at pH 5.2, compared to pH 5.5 and pH 6.0, demonstrating that the stability of the long-acting hGH conjugate in the buffer with a pH of 5.2 was improved (FIG. 1). The impurities were analyzed by peptide mapping, followed by determining molecular weights through LC-MS/MS. Impurity #6 and #7 were determined to be deaminated impurities.

Example 5

Assay of Long-Acting hGH Conjugate for Stability in Relation to Non-Ionic Surfactant After being stored at 25° C. for four weeks in a formulation comprising the non-ionic surfactant polysorbate 80 or 20, or poloxamer 188 as a stabilizer, the stability of the long-acting hGH was assayed using SEC and IEC. In the formulation, as seen in Table 7, pH 5.2 citric acid buffer and mannitol were used as the buffer and sugar alcohol, respectively. In Table 8, IE-HPLC (%) and SE-HPLC (%) revealed the residual purity of the long-acting hGH conjugate in comparison with initial purity.

TABLE 7

| No. | Conc. | Buffer | Salt | Sugar Alcohol | Surfactant |
|---|---|---|---|---|---|
| 1 | 19.5 mg/mL | 20 mM Na-Citrate (pH 5.2) | 150 mM NaCl | 5% Mannitol | 0.05 mg/mL Polysorbate 80 |
| 2 | 19.5 mg/mL | 20 mM Na-Citrate (pH 5.5) | 150 mM NaCl | 5% Mannitol | 3 mg/mL Poloxamer 188 |
| 3 | 19.5 mg/mL | 20 mM Na-Citrate (pH 5.2) | 150 mM NaCl | 5% Mannitol | 2 mg/mL Polysorbate 20 |

* 0.05 mg/mL Polysorbate 80 corresponds to 0.005% Polysorbate 80.

TABLE 8

| | IE-HPLC (%) | | | | SE-HPLC (%) | | | |
|---|---|---|---|---|---|---|---|---|
| No. | Start | 1 week | 2 weeks | 4 weeks | Start | 1 week | 2 weeks | 4 weeks |
| 1 | 100 | 98.0 | 96.4 | 93.3 | 100 | 99.6 | 99.5 | 99.3 |
| 2 | 100 | 98.3 | 85.8 | N/A$^A$ | 100 | 100 | 95.3 | N/A$^A$ |
| 3 | 100 | 98.3 | 96.4 | 84.8 | 100 | 99.7 | 99.9 | 96.3 |

$^A$data was not available due to the precipitation by aggregation

As understood from the data, the stability of the long-acting hGH conjugate was observed to increase in the presence of polysorbate 80. In the case of polysorbate 20, no differences from polysorbate 80 were detected in the stability of the long-acting conjugate until two weeks, but after storage for four weeks, there was a significant difference in the stability therebetween although they were very similar to each other. In addition, the long-acting hGH conjugate aggregated after storage at 25° C. for two weeks in the formulation containing 2 mg/mL poloxamer 188.

Example 6
Comparison of Stability Between the Liquid Long-Acting hGH Conjugate and the Commercially Available Drug Norditropin The stabilization ability of the formulation composed of citrate buffer pH 5.2, NaCl, mannitol and polysorbate 80, finally selected through the stability assays of Examples 2 to 5, was evaluated by comparison with the commercially available liquid hGH formulation Norditropin (Novo Nordisk). Norditropin has a concentration of 10 mg/mL and its ingredients are given in Table 9, below. They were stored at 25° C. for four weeks. To confirm a diversity of charges, Norditropin was assayed using capillary electrophoresis (CE) and SEC as described in the European Pharmacopoeia. On the other hand, the long-acting hGH conjugate of the present invention was analyzed using IEC and SEC, which are similar in principle to the CE assay. The results are given in Table 10, below. CE (%), or IE-HPLC (%) and SE-HPLC (%) exhibit the residual purity of the long-acting hGH conjugate in comparison with initial purity.

TABLE 9

| Formulation | Conc. | Buffer | Salt and others | Sugar alcohol and others | Surfactant |
|---|---|---|---|---|---|
| Norditropin | 10 mg/mL | — | 3 mg/mL Phenol | 1.13 mg/mL Histidine 38.7 mg/mL Mannitol | 3 mg/mL Poloxamer 188 |
| Long-Acting hGH | 19.5 mg/mL (6 mg/mL hGH) | 20 mM Na-Citrate (pH 5.2) | 150 mM NaCl | 5% Mannitol | 0.005% Polysorbate 80 |

TABLE 10

| | CE (%) or IEC (%) | | | | SEC (%) | | | |
|---|---|---|---|---|---|---|---|---|
| No. | Start | 1 week | 2 weeks | 4 weeks | Start | 1 week | 2 weeks | 4 weeks |
| Norditropin | 100 | 98.2 | 95.9 | 91.5 | 100 | 100 | 100.1 | 100 |
| Long-acting hGH | 100 | 98.0 | 96.4 | 93.3 | 100 | 99.6 | 99.5 | 99.3 |

As can be seen, the formulation of the present invention guaranteed the stabilization of hGH at a level as high as or higher than can the commercially available hGH formulation Norditropin. These results demonstrate that the liquid formulation of long-acting hGH of the present invention can provide excellent storage stability for hGH.

Example 7

Assay of the Liquid Long-Acting hGH Conjugate for Long-Term Storage Stability

Figure 2:
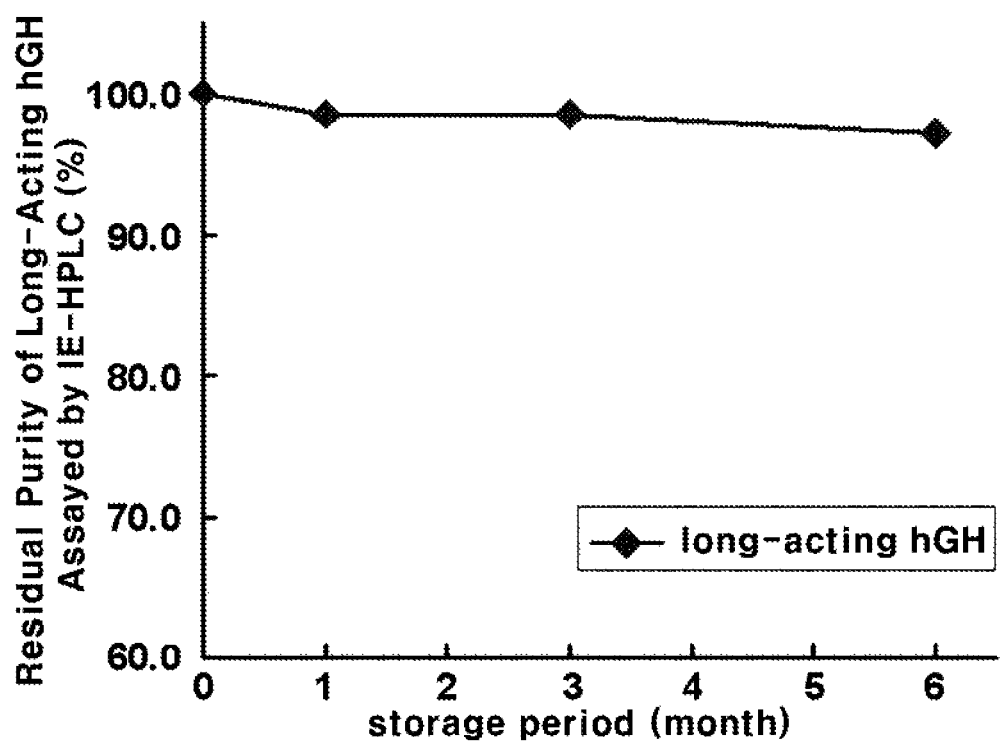
FIG. 2 is a graph obtained after analyzing the stability of a long-acting hGH conjugate with IE-HPLC during the storage thereof at 4° C. for six months in a buffer at a pH of 5.2 as described in Example 7.

To evaluate the long-term storage stability of the liquid formulation composed of citric acid buffer pH 5.2, NaCl, mannitol and polysorbate 80, the samples were analyzed for stability after storage at 4° C. for six months in the formulation. The results are given in FIG. 2 and Table 11. IE-HPLC (%), SE-HPLC(%), and protein contents (%) reveal the residual purity of the long-acting hGH conjugate in comparison with initial purity.

TABLE 11

Test of Long-Term Storage Stability (Storage at 4° C.)

| | | Identification Test | | | Purification Test | | Protein | |
|---|---|---|---|---|---|---|---|---|
| Storage Period | Property | pH | IE-HPLC | Western Blot | SDS-PAGE | IE-HPLC(%) | SE-HPLC(%) | Content (%) | Biological activity |
| Start | Colorless | 5.3 | Confirmed | Confirmed | Confirmed | 100.0 | 100.0 | 100.0 | Confirmed |
| 1 Month | Colorless | 5.3 | Confirmed | Confirmed | Confirmed | 98.5 | 99.9 | 104.2 | Confirmed |
| 3 Months | Colorless | 5.3 | Confirmed | Confirmed | Confirmed | 98.5 | 100.0 | 104.5 | Confirmed |
| 6 Months | Colorless | 5.3 | Confirmed | Confirmed | Confirmed | 97.2 | 99.3 | 101.9 | Confirmed |

The long-acting hGH conjugate of the present invention was observed to be stable for more than 6 months in the liquid formulation.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A liquid formulation of a long-acting human growth hormone conjugate, comprising
   a pharmaceutically effective amount of the long-acting human growth hormone conjugate in which the human growth hormone and an immunoglobulin Fc region are linked to each other via a polyethylene glycol; and
   an albumin-free stabilizer, said stabilizer consisting essentially of a buffer of pH 5.0-6.0, a sugar alcohol, a polysorbate as a non-ionic surfactant and sodium chloride as a tonicity agent.

2. The liquid formulation of the long-acting human growth hormone conjugate of claim 1, wherein the sugar alcohol is selected from the group consisting of mannitol, sorbitol and a combination thereof.

3. The liquid formulation of the long-acting human growth hormone conjugate of claim 1, wherein the sugar alcohol is used in an amount of from 1 to 10% (w/v) based the total volume of the formulation.

4. The liquid formulation of the long-acting human growth hormone conjugate of claim 1, wherein the buffer is a citrate or phosphate buffer.

5. The liquid formulation of the long-acting human growth hormone conjugate of claim 1, wherein the buffer ranges in pH from 5.2 to 6.0.

6. The liquid formulation of the long-acting human growth hormone conjugate of claim 1, wherein the buffer ranges in pH from 5.2 to 5.5.

7. The liquid formulation of the long-acting human growth hormone conjugate of claim 1, wherein the sodium chloride is used in a concentration of from 5 to 200 mM.

8. The liquid formulation of the long-acting human growth hormone conjugate of claim 1, wherein the polysorbate is polysorbate 80.

9. The liquid formulation of the long-acting human growth hormone conjugate of claim 1, wherein the polysorbate is used in an amount of from 0.001 to 0.05% (w/v) based on the total volume of the formulation.

10. A liquid formulation of a long-acting human growth hormone conjugate comprising
    a pharmaceutically effective amount of the long-acting human growth hormone conjugate in which the human growth hormone and an immunoglobulin Fc region are linked to each other via a polyethylene glycol; and
    an albumin-free stabilizer, said stabilizer consisting essentially of a buffer of pH 5.0-6.0, a sugar alcohol, a polysorbate as a non-ionic surfactant, sodium chloride as a tonicity agent, and one or more ingredient selected from the group consisting of a sugar, a polyalcohol and an amino acid.

11. The liquid formulation of the long-acting human growth hormone conjugate of claim 1, wherein the human growth hormone and the immunoglobulin Fc region are linked to each other via a polyethylene glycol, and the stabilizer consisting essentially of a citrate buffer with a pH of 5.2 to 6.0, 1-10% (w/v) mannitol, 0.001-0.05% polysorbate 80, and 5-200 mM NaCl.

12. The liquid formulation of the long-acting human growth hormone conjugate of claim 1, wherein the human growth hormone has an amino acid sequence identical to that of a native human growth hormone.

13. The liquid formulation of the long-acting human growth hormone conjugate of claim 1, wherein the immunoglobulin Fc region is selected from the group consisting of an Fc region of IgG, IgA, IgD, IgE, and IgM.

14. The liquid formulation of the long-acting human growth hormone conjugate of claim 13, wherein the immunoglobulin Fc region is a dimer or multimer of a single stranded immunoglobulin having domains of the same origin.

15. The liquid formulation of the long-acting human growth hormone conjugate of claim 13, wherein the immunoglobulin Fc region is an IgG4 Fc region.

16. The liquid formulation of the long-acting human growth hormone conjugate of claim 15, wherein the immunoglobulin Fc region is an aglycosylated human IgG4 Fc region.

17. The liquid formulation of the long-acting human growth hormone conjugate of claim 1, wherein the long-acting human growth hormone conjugate comprises a human growth hormone and an immunoglobulin Fc region with a linkage via a non-peptidyl polymer.

18. The liquid formulation of the long-acting human growth hormone conjugate of claim 17, wherein the non-peptidyl polymer is selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, polylactic acid, polylactic-glycolic acid, lipid polymers, chitins, hyaluronic acid, and a combination thereof.

19. A method for producing the liquid formulation of the long-acting human growth hormone conjugate as in one of claims 1-6, 7-13, and 14-18, comprising:
    combining the long-acting human growth hormone conjugate with a stabilizer, said stabilizer consisting essentially of a buffer with a pH of 5.0-6.0, a sugar alcohol, a polysorbate as a non-ionic surfactant and sodium chloride as a tonicity agent to give the liquid formulation comprising the long-acting human growth hormone conjugate and the stabilizer.

20. A method for stabilizing a long-acting human growth hormone conjugate according to claim 1 in a liquid formulation comprising the long-acting human growth hormone conjugate, said method comprising:
    combining the long-acting human growth hormone conjugate with a stabilizer, said stabilizer consisting essentially of a buffer with a pH of 5.0-6.0, a sugar alcohol, a polysorbate as a non-ionic surfactant and sodium chloride as a tonicity agent to obtain the liquid formulation comprising the long-acting human growth hormone conjugate and the stabilizer, said liquid formulation retains the activity of the long-acting human growth hormone conjugate at a level of 90% or greater of the original activity after storage at 40±2° C. for one weeks.

21. The liquid formulation of the long-acting human growth hormone conjugate of claim 1, wherein the polysorbate is used in an amount of from 0.001 to 0.01% (w/v) based on the total volume of the formulation.

* * * * *